United States Patent [19]

Smith

[11] Patent Number: Plant 5,423

[45] Date of Patent: Mar. 26, 1985

[54] GARDINER PEACH TREE

[76] Inventor: Ronald E. Smith, Rte. 1, Box 347D, Leesburg, Va. 22075

[21] Appl. No.: 530,260

[22] Filed: Sep. 8, 1983

[51] Int. Cl.[3] ..... A01H 5/03

[52] U.S. Cl. ..... Plt./43

[58] Field of Search ..... Plt./43

*Primary Examiner*—Robert E. Bagwill

[57] ABSTRACT

A variety of peach tree which is of large size, vigorous spreading growth, being a productive and regular bearer of large size, firm, yellow-flesh, freestone fruit having yellow skin substantially overspread with red. The fruit is further characterized by its good eating, canning and stowage quality.

1 Drawing Figure

ORIGIN OF THE VARIETY

The new variety of peach tree was discovered by me in my orchard located near Leesburg, Va., the result of a seed planted by me in 1968.

ASEXUAL REPRODUCTION OF THE VARIETY

The present variety of peach tree was asexually propagated by budding and grafting, as performed by me in my orchard and such reproductions run true to the original tree in all respects.

SUMMARY OF THE VARIETY

The herein claimed variety of peach tree is of large size, vigorous, spreading in growth, and a productive and regular bearer of large size, late ripening, freestone fruit having firm, yellow flesh and a high degree of red skin color.

PHOTOGRAPHS OF VARIETY

The accompanying photographs show typical specimens of the foliage and fruit of my new variety, with the upper surface of the foliage being illustrated and including a fruit divided on its suture plane to reveal flesh coloration and showing a stone remaining in place.

DESCRIPTION OF THE VARIETY

The botanical details of this new and distinct variety of peach tree are as follows, with color terminology (except those in common terms) in accordance with The R.H.S. Colour Chart.

TREE

Size: Large.
Vigor: Vigorous.
Form: Spreading.
Production: Productive.
Density: Open.
Bearing: Regular.

TRUNK

Size: Stocky.

BRANCHES

Size: Stocky.
Lenticels: Medium size. Medium number.
Texture: Medium rough.

LEAVES

Size:
*Average length.*—6".
*Average width.*—$1\frac{1}{4}$".
Form: Lanceolate. Acutely pointed.
Color:
*Upper surface.*—Near 137B.
*Lower surface.*—Near 138A.
Margin: Crenate.
Texture: Smooth.
Petiole: Medium length.
Glands: Not prominent.

FLOWER BUDS

Size: Small.
Length: Short.

FLOWERS

Blooming period: April 4 to April 24. Average April 14th.
Size: Small, not showy.

FRUIT

Maturity when described: Hard ripe.
Date of first picking: August 24th.
Date of last picking: September 3rd.
Size: Comparatively uniform. Large, up to one pound.
*Average diameter axially.*—$3\frac{1}{4}$".
*Average transversely in suture plane.*—3".
Form: Oblong, pointed.
Suture: Very shallow, extends from base to apex.
Ventral surface: Rounded, varies from equal to unequal.
Cavity: Rounded.
*Average depth.*—$\frac{1}{4}$".
*Average breadth.*—$\frac{3}{4}$".
Apex: Short.

SKIN

Thickness: Thin.
Texture: Not tenacious to flesh.
Tendency to crack: Slight.
Down: Wanting.
Color: Yellow ground color (16B) to (16C). Red blush covering half the surface (44C) to (45C).

FLESH

Juice: Moderate.
Texture: Firm, meaty.

Ripens: Even.
Flavor: Subacid.
Aroma: Pronounced.
Eating quality: Excellent.
Canning quality: Excellent.
Color: Yellow-orange near (15C) to (17C).
Cavity color: Near 44C and extends into flesh.

STONE

Type: Freestone.
Fibers: Few, long.
Size: Medium.
*Average length.*—$1\frac{3}{4}''$.
*Average width.*—$1''$.
*Average thickness.*—$\frac{5}{8}''$.
Form: Elongated, tip short.
Base: Blunt pointed.
Sides: Mostly equal.

Surfaces: Furrowed from base to apex, pitted toward apex.
Color: Near 173B, occasionally streaked reddish purple.
Tendency to split: Slight.

USE

Fresh — canning.

KEEPING QUALITY

Very good.

The following is claimed:

1. A new and distinct variety of peach tree, as illustrated and described, which is a regular and productive bearer of large size, freestone fruit, with firm flesh, attractive skin, having an attractive red blush color and of good fresh eating and canning quality.

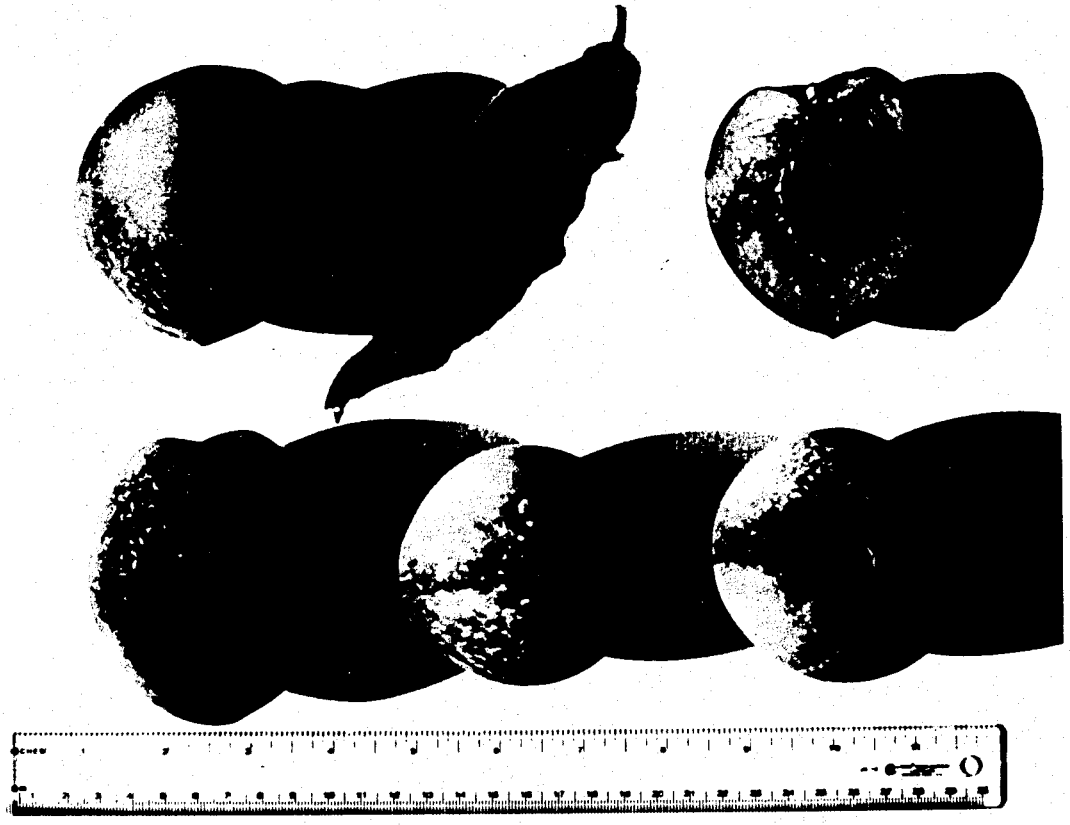

* * * * *